United States Patent [19]
Koudijs et al.

[11] Patent Number: 5,438,194
[45] Date of Patent: Aug. 1, 1995

[54] ULTRA-SENSITIVE MOLECULAR IDENTIFIER

[75] Inventors: Reijer Koudijs, Kootwijkerbroek; Marcel M. Mulder, Duivendrecht, both of Netherlands; Kenneth H. Purser, Lexington, Mass.; Frans W. Saris, Amsterdam, Netherlands

[73] Assignee: High Voltage Engineering Europa B.V., Amersfoort, Netherlands

[21] Appl. No.: 99,844

[22] Filed: Jul. 30, 1993

[51] Int. Cl.[6] .......................................... H01J 49/26
[52] U.S. Cl. ........................................ 250/288; 250/282
[58] Field of Search ............... 250/288 A, 423 R, 288, 250/282

[56] References Cited

U.S. PATENT DOCUMENTS

| | | | |
|---|---|---|---|
| 3,617,789 | 11/1971 | Middleton et al. | 250/423 R |
| 3,786,249 | 1/1974 | Anbar et al. | 250/288 A |
| 4,037,100 | 7/1977 | Purser | 250/281 |

OTHER PUBLICATIONS

Science, vol. 236, p. 543–550 (1987) D. Elmore, et al. "Accelerator Mass Spectrometry"n.
Proc. Nat. Acad. Science USA, vol. 87, pp. 5288–5292 (1990) K. W. Turtletaub, et al.
Biochem J., vol. 35, pp. 1358–1368 (1941) A. J. P. Martin et al. (Liquid Chromatography).
Nucl. Instr. and Meth., vol. 214, pp. 139–150 (1983), R. Middleton.
Nuc. Instr. and Meth., vol. B52 pp. 322–326 (1990, C. R. Bronk and R. E. M. Hedges.
Nuclear Inst. and Meth., vol. 162, pp. 637–656 (1979), K. H. Purser, et al.

*Primary Examiner*—Jack I. Berman
*Attorney, Agent, or Firm*—Nields & Lemack

[57] ABSTRACT

Samples are directed into a liquid or gas chromatograph, and the output from the liquid or gas chromatograph is directed into the ion source of an accelerator mass spectrometry system so as to provide an ultra-sensitive identifier of molecules in the samples.

14 Claims, 4 Drawing Sheets

ULTRA-SENSITIVE MOLECULAR IDENTIFIER

BACKGROUND OF THE INVENTION

1. Field of the invention

This invention relates to the field of trace molecule identification wherein molecules that are found to have been tagged with a tracer radioactive atom or rare stable isotope are catalogued according to their molecular structure. Although limitations in scope are not intended, this invention has particular relevance to the fields of biomedicine and biochemistry.

2. Description of the Prior Art

During the last fifteen years widespread interest has developed in a new mass spectrometer technique that uses an MeV accelerator as one element of a double mass spectrometer. This technique has been described, for example, in U.S. Pat. No. 4,037,100 to K. H. Purser and in an article entitled "Accelerator Mass Spectrometry" by D. Elmore and F. M. Phillips in *Science* at volume 236, pages 543–550 (1987). This technique, known as Accelerator Mass Spectrometry (AMS), has demonstrated the capability of measuring isotopic ratios as low as $1:10^{15}$ for many rare and radioactive isotopes and is one of the most sensitive analytical techniques available today. The reasons AMS achieves up to six orders of magnitude improvement in isotopic ratio sensitivity compared to that which is achievable using conventional mass spectroscopy are: (1) molecular interferences can be eliminated by fragmentation; (2) there are substantial reductions in small angle scattering; (3) Energy/Charge ambiguities are no longer an issue because direct measurements of kinetic energy become possible.

The first attempt to integrate AMS with biological procedures started in 1988 when workers used AMS to explore the role that xenobiotics play in initiating mutations. This attempt is described in an article entitled "Accelerator Mass Spectrometry in Biological Dosimetry. Relation between low-level exposure and covalent binding of heterocyclic amine carcinogens to DNA" by K. W. Turtletaub, J. S. Felton, J. S. Gledhill, J. R. Vogel, J. R. Southern, M. W. Caffee, M. W. Finkel, D. E. Nelson, I. P. Proctor and J. C. Davis in *Proc. Nat. Acad. Science USA* at volume 87 page 5288 (1990). With radiocarbon ($^{14}$C) as a tracer, the above referenced workers used hosts, which included cell lines, rodents and primates, to detect the effects of toxins, mutagens, carcinogens and chemical therapeutics in living systems. The usefulness of $^{14}$C is that it can be incorporated into most organic molecules. Furthermore, the site of the introduced radiocarbon atom can be accurately specified by the production procedure and located within the molecule at sites that are not subject to exchange. Compared to the scintillation counting method, this application of AMS to biology has resulted in a 6 order-of-magnitude increase in tracer detection sensitivity.

While such measurements are extremely sensitive and allow many new types of measurement, they provide no structural information about the molecule where the $^{14}$C finally resides. No knowledge is available from such measurements whether the $^{14}$C label is attached to the same compound that was administered at the beginning of a test or whether the original chemical has been modified by some metabolic process.

The present invention describes an analysis method that overcomes the above shortcoming. The method provides structural information while still retaining the high sensitivity of AMS.

SUMMARY OF THE INVENTION

The present invention relates to a method of analysis that classifies those molecules carrying a suitable tag according to their molecular structure. While $^{14}$C is the tag of choice for many biological measurements, and its use is assumed in the following description, the technique is not limited to this nuclear species.

In essence, technique of the present invention includes a liquid or gas chromatograph that is coupled directly to the input of an AMS analyzer. The transit time of the sample through a chromatograph is dependent upon the molecular species, so that at the exit, individual components of a complex mixture are dispersed in time. When AMS measurements are made simultaneously, only those chromatographic peaks will be recorded that are also associated with high counting rates of $^{14}$C.

The important features of this invention for biochemistry and biomedicine are:

1. Because of the high efficiency of AMS for detecting $^{14}$C, the necessary sample size is small. Thus, a large number of samples can be taken for following time-dependent processes.
2. Metabolic changes can be followed because of the chromatographic molecular identification.
3. The counting rates are sufficiently high that count-rate changes of a few percent can be measured quickly and with statistical precision. Thus, very low concentrations of trace chemicals are needed.
4. The high counting rate for $^{14}$C implies that even if the contribution by the tagged molecules to an existing chemical channel is small, the concentration of these tagged molecules can be measured quantitatively.
5. Because of the high sensitivity, the necessary radioactivity is small and the question of nuclear waste disposal becomes a nonissue. Incineration followed by stack gas dilution can be responsibly employed to produce a released activity that is below the concentration of $^{14}$C in the atmosphere.
6. Compared to the natural activity of $^{14}$C in the human body ($\sim 10$ nCi), the introduced radioactivity can be small ($\sim 1$ nCi).

BRIEF DESCRIPTION OF THE DRAWINGS

The invention may best be understood from the following detailed description thereof, having reference to the accompanying drawings, in which.

DESCRIPTION OF THE PREFERRED EMBODIMENT

Figure 1:
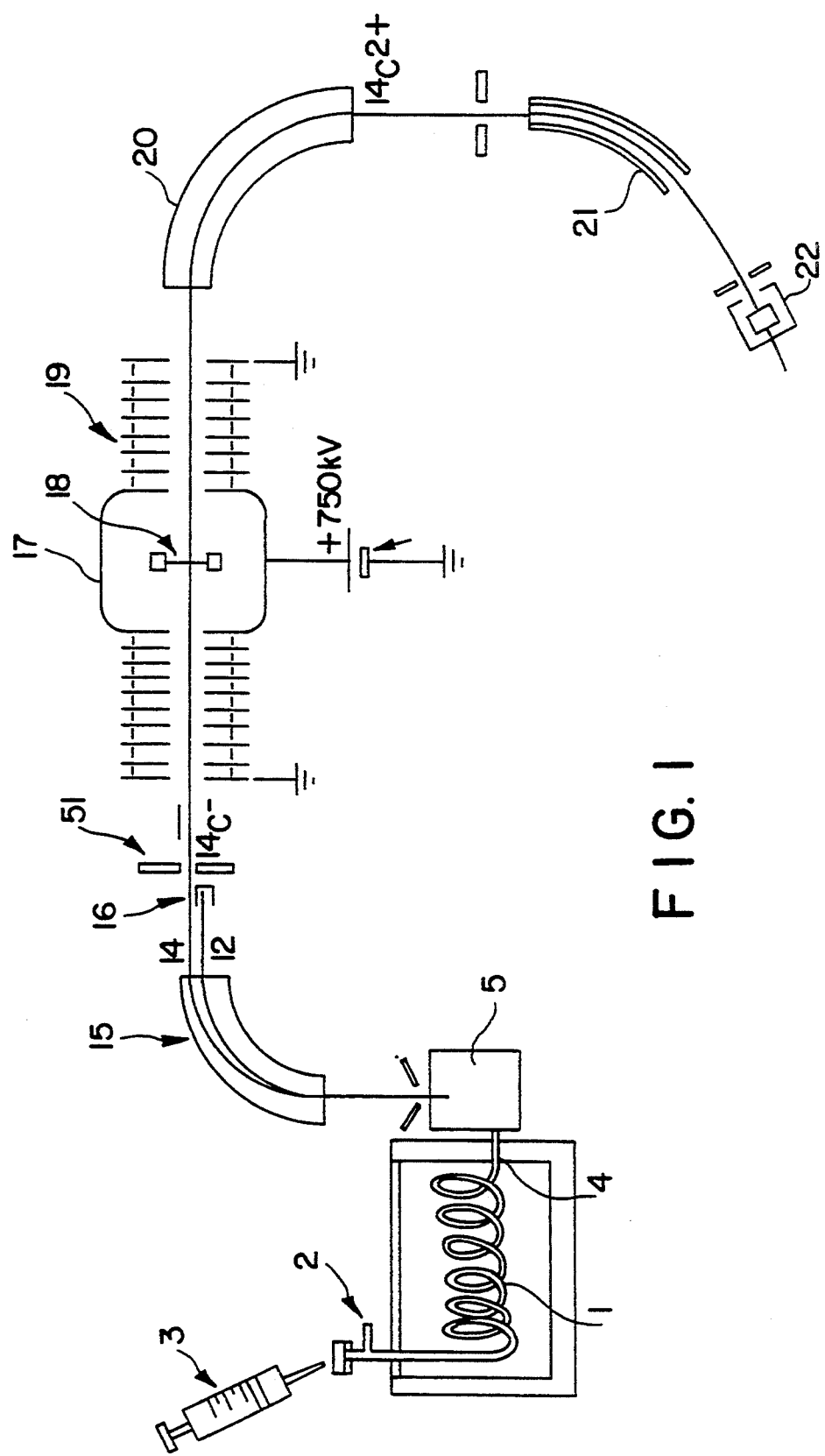
FIG. 1 is a schematic diagram showing the arrangement of the ultra-sensitive molecular identifier of the present invention.

Referring to the drawings, and first to FIG. 1 thereof, therein is shown a typical arrangement of the ultra-sensitive molecular identifier of the present invention. The arrangement includes a chromatographic stage, an ion source stage, and an AMS section.

The chromatographic stage

In the chromatographic stage either liquid or gas chromatography can be used. For many applications liquid chromatography (LC), described, for example, by A. J. P. Martin and R. L. M. Synge in volume 35 of *Biochem J.* at page 1358 (1941), is more appropriate as the first section of the disclosed ultra-sensitive molecular identifier because the derivatization needed to produce volatile compounds for gas chromatography is often difficult. A larger range of compounds can be dissolved to provide separation on an LC column.

Gas chromatography (GC) is described, for example, in "Biochemical Applications of Gas Chromatography" by H. P. Burchfield and E. Starrs (Academic Press, Inc., New York (1962), and, as shown in FIG. 1, the method is based upon a long capillary tube 1 the inner wall of which is coated with a thin film of so-called stationary phase. This GC column is flushed continuously with a carrier gas entering the capillary tube 1 through a gas inlet 2, so that molecules including those to be identified which are injected in a burst at one end of the column, using a syringe 3 or pyrolysis are transported to the chromatograph exit 4. By choosing an appropriate temperature and stationary phase, the transit speed of the wanted molecular species can be chosen to be different from the other components present in the input burst and hence the wanted molecules exit the column at a different time from other species.

The ion source stage

Negative ions are needed by the AMS tandem. It can be seen from FIG. 1 that the output from the chromatograph section of the instrument couples directly to the ion source system 5. Here the incoming molecules are dissociated to produce carbon atoms that are either converted to $C^-$ at a cesiated surface or alternatively to $C^+$ ions that are accelerated to an energy $\sim 20$ keV. At this energy $C^+$ ions can be efficiently converted to $C^-$ by charge exchange in an external vapor canal.

For those skilled in the art it will be clear that a variety of ion source designs can be adapted to carry out the above tasks. Three possible designs will be described.

Figure 2:
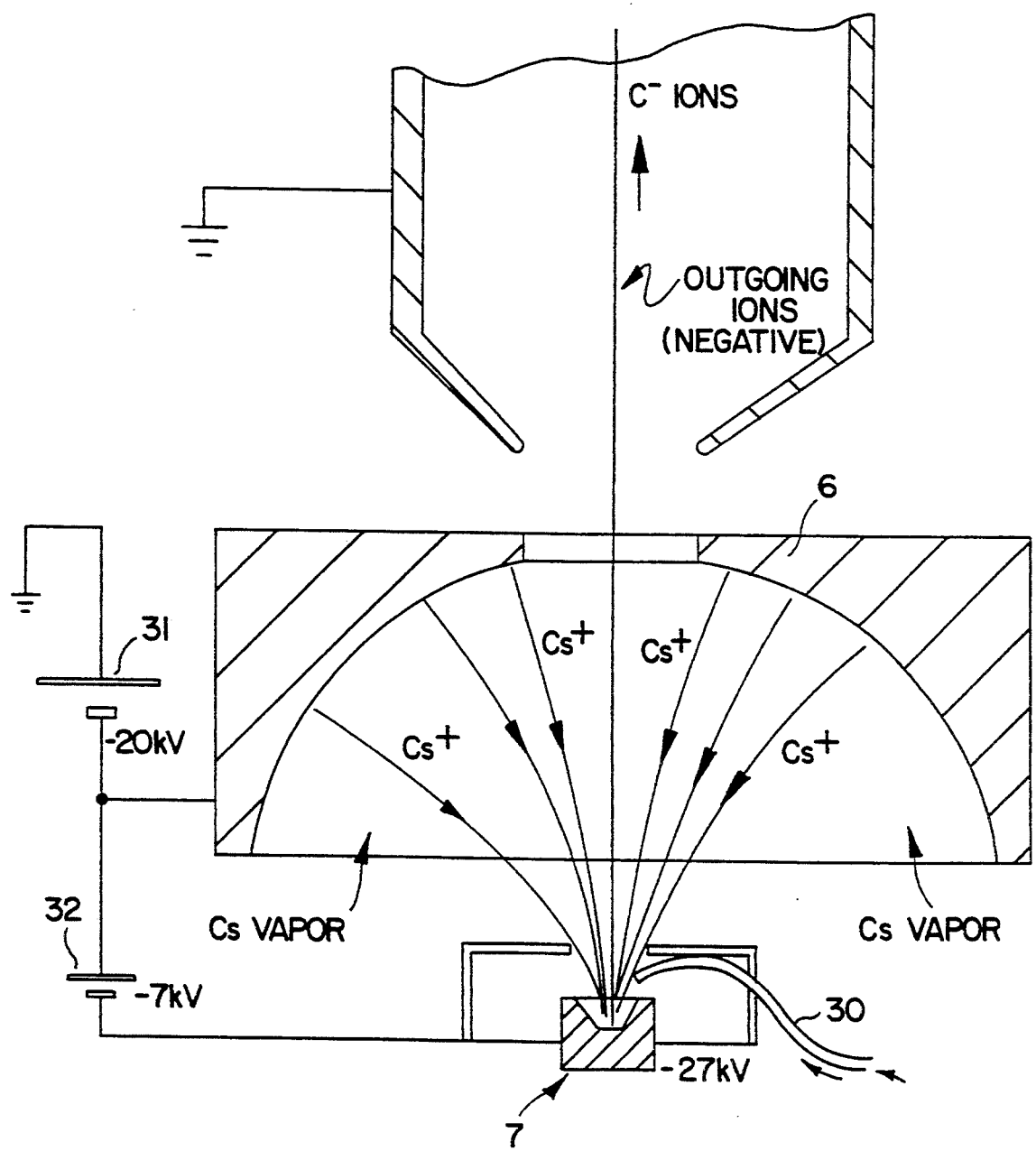
FIG. 2 is a schematic diagram on an enlarged scale showing one type of C$^-$ ion source system suitable for use in the apparatus of FIG. 1.

The first is to use a molecular dissociator/converter based upon the negative ion sources that have been developed at the University of Pennsylvania and Oxford, as described, for example, in the article by R. Middleton entitled "A Negative Ion Cesium Sputter Ion Source" at volume 214 of *Nucl. Instr. and Meth.*, page 139 (1983) and in the article by C. R. Bronk and R. E. M. Hedges entitled "A Negative Ion Source for Routine AMS Radiocarbon Dating" at volume B52 of *Nucl. Inst. and Meth.*, pages 322–326 (1990), respectively. The preferred embodiment, which is shown in FIG. 2, includes a source of cesium ions ionized by a heated sintered tungsten spherical ionizer 6. The ionizer 6 is maintained at $\sim 1000°$ C. and when cesium (Cs) vapor strikes the hot tungsten surface it becomes ionized. The resulting $Cs^+$ ions are accelerated to strike or bombard a titanium cone 7 onto which the time sequenced molecular effluent (including the unknown molecules) from the chromatograph column is deposited by being sprayed thereon after arriving through the conduit 30. The incoming Cs ions fragment the unknown molecules, some of which leave the surface of the titanium cone 7 with a negative charge. That is to say, the incoming cesium ions serve the dual function of dissociating the arriving molecules together with the formation of a low work function monolayer that donates electrons to the electronegative carbon ions as they leave the surface. Because samples may vary greatly in their concentrations of $^{14}C$ it is desirable to be able to change the titanium inserts (i.e. the titanium surfaces of the cone 7) between measurements.

As shown in FIG. 2, the sintered tungsten spherical ionizer 6 is maintained at about $-20$ kV with respect to ground by a voltage source 31 and the titanium cone 7 is maintained at about $-7$ kV with respect to the spherical ionizer 6 by a voltage source 32, so that the titanium cone is at a voltage of about $-27$ kV with respect to ground.

Figure 3:
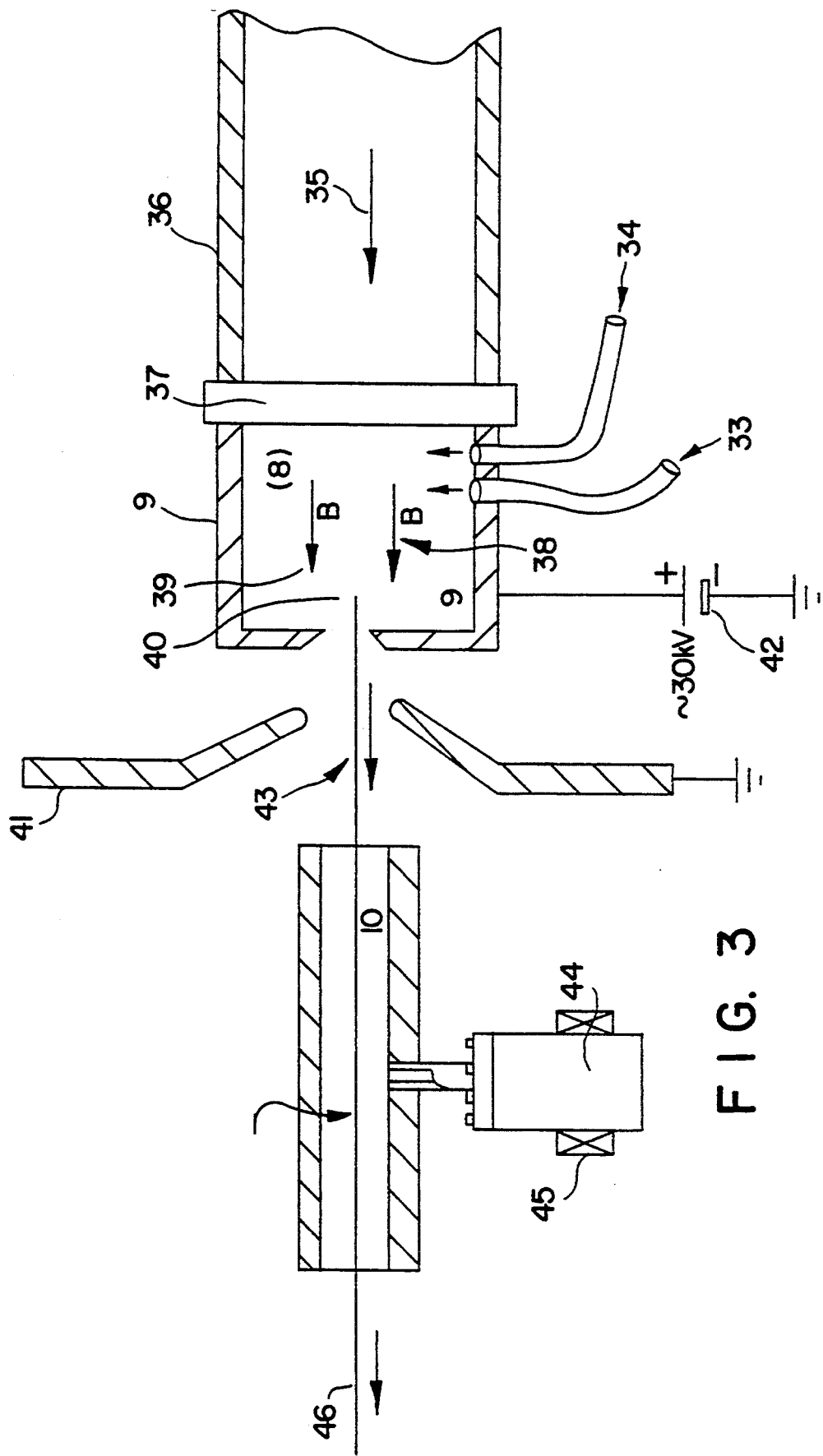
FIG. 3 is a schematic diagram, similar to that of FIG. 2, showing another type of C$^-$ ion source system suitable for use in the apparatus of FIG. 1.

A second embodiment for the ion source system is shown schematically in FIG. 3 and includes an axial magnetic field microwave or radio frequency ion source system 8. Such sources do not require filaments, and can operate continuously for very long periods of time with little maintenance. Oxygen gas is introduced from an oxygen gas supply 33 to an arc chamber 9 to maintain a discharge. Here, the electron density is high and induces dissociation of the molecules leaving the chromatograph column through the input 34 from the chromatograph. Positive ions can be extracted from the arc chamber 9, and these positive ions are then charge-exchanged in a vapor charge exchange canal 10. One reason for choosing oxygen is that any residual carbon will be rapidly converted to $CO_2$ in which form it can be rapidly pumped away. The reaction involved is as follows:

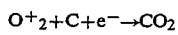

$$O^+{}_2 + C + e^- \rightarrow CO_2$$

As shown in FIG. 3, the incoming microwave power is indicated by the arrow 35 and is conveyed by a waveguide 36 which terminates in a vacuum window 37 for microwaves at the boundary with the arc chamber 9. The magnetic field in the arc chamber 9 is indicated by the arrows 38. The oxygen plasma within the arc chamber 9 is indicated at 39, and the electron bombardment region within the arc chamber 9 is indicated at 40. An extraction electrode 41 is grounded, and the arc chamber 9 is maintained at about $+30$ kV by a voltage source 42, thus providing the extraction voltage. The positive ion region is indicated at 43. The charge-changing canal 10 is filled with lithium or sodium vapor generated in a sodium or lithium boiler 44 energized by a heater 45. The outgoing beam containing a mixture of positive, neutral and negative ions is indicated at 46.

Figure 4:
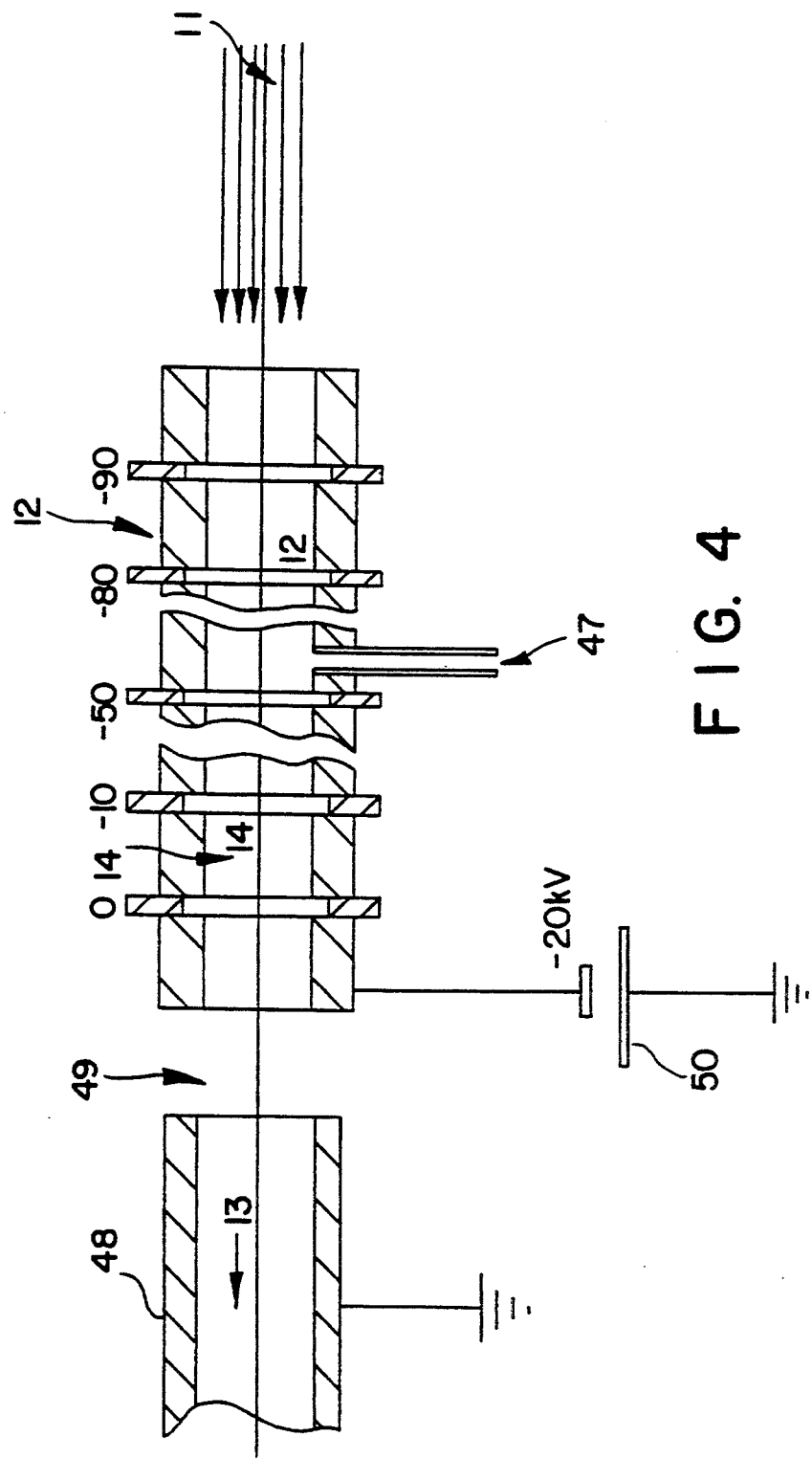
FIG. 4 is a schematic diagram, similar to that of FIG. 2, showing still another type of C$^-$ ion source system suitable for use in the apparatus of FIG. 1.

A third possibility for the ion source system is shown in FIG. 4. An intense beam of ions 11 having an energy of $\sim 20$ keV is directed along the length of a graded canal 12 or tube at elevated potential, into the center of which the molecular effluent from the chromatograph column is directed through the conduit 47. The incident ions serve to dissociate the incoming molecules. Negative ions 13 are produced in the dissociation process, and these negative ions 13 drift along the length of the tube 12 under the influence of an axial electric field 14. Such a device is particularly suitable for liquid chromatography applications because large pumps can be used to evaporate the liquid without introducing source poisoning in an arc chamber.

As shown in FIG. 4, the emerging negative ions 13 are directed into a grounded tube 48 across an acceleration gap 49 by virtue of the voltage source 50 which maintains the output end of the graded canal 12 at a voltage of −20 kV with respect to ground. In addition to the methods of dissociation disclosed in connection with the aforementioned three possible designs for the ion source stage, the molecules present in the output of the chromatographic column may be dissociated by high temperature pyrolysis.

The AMS section

As mentioned in the foregoing description of the ion source stage, the AMS analyzer requires negative ions from the ion source system. These ions are dispersed by a magnetic spectrometer 15 or analysis magnet that (in cooperation with a mass-14 defining aperture 51) selects mass-14 particles for injection into the tandem. The associated mass-12 ions are collected for normalization in a separate Faraday cup 16 before tandem acceleration.

While it will be clear to those skilled in the art that a wide range of terminal voltages can be used for tandem acceleration, in the preferred embodiment of the present invention the selected mass-14 ions are attracted to a 0.75 MV positive high voltage terminal 17. Within the terminal 17 the ions pass through a thin stripper foil 18 or gas cell that induces electron stripping and molecular dissociation of any background molecules. All ions and charge states are accepted by the second stage of acceleration 19. However, in the preferred embodiment of the invention, the high energy mass analyzer 20 would only accept 2+ ions that will have a final energy of 2.25 MeV.

The ions leaving the tandem accelerator will be analyzed by both a magnetic analyzer 20 and electrostatic analyzer or bend 21. Such a combination defines a single point in E/q and M/q space, as is explained in the article by K. H. Purser, A. E. Litherland and H. E. Gove entitled "Ultra Sensitive Accelerator Mass Spectrometry" in volume 162 of *Nuclear Instr. and Meth.* at page 637 (1979). It will be clear to those skilled in the art that other arrangements of electromagnetic constraints can also provide the necessary definition.

The accelerated ions will be stopped in an energy detector 22 where a pulse proportional to energy and/or rate of energy loss will be derived for each particle. It will be clear to those skilled in the art that the height of such pulses can be used to select wanted events and reject backgrounds. While the preferred embodiment for the detector is a solid state device, those skilled in the art will recognize that there is a choice of adequate detectors, which include gas detectors, that can be used to measure both kinetic energy and the rate of energy loss.

Having thus described the principles of the invention, together with illustrative embodiments thereof, it is to be understood that, although specific terms are employed, they are used in a generic and descriptive sense, and not for purposes of limitation, the scope of the invention being set forth in the following claims.

We claim:

1. A method for identifying and detecting molecules which have been labeled by a specific radioisotope or stable isotope, comprising the following steps: (1) separating various molecules in a sample by use of a chromatographic column, (2) coupling the output of said column directly into an ion source system where the molecules present in the said output are dissociated and negative ions produced, (3) directing said negative ions into a tandem accelerator mass spectrometer, thereby forming positive ions having high velocity, and (4) stopping said positive ions in a particle detector.

2. A method in accordance with claim 1 wherein said specific radioisotope is carbon-14.

3. Apparatus for identifying and detecting molecules which have been labeled by a specific radioisotope or stable isotope, comprising in combination: (1) a chromatographic column for separating various molecules in a sample, (2) an ion source system for producing negative ions, (3) means for coupling the output of said column directly into said ion source system, (4) means within said ion source system for dissociating the molecules present in the said output, (5) a tandem accelerator mass spectrometer, (6) means for directing said negative ions into said tandem accelerator mass spectrometer, thereby forming positive ions having high velocity, and (7) a particle detector adapted to stop said positive ions.

4. Apparatus in accordance with claim 3 wherein the said chromatographic column employs liquid as the moving phase and a solid or a liquid on a solid support as the stationary phase.

5. Apparatus in accordance with claim 3 wherein the said chromatographic column is a gas chromatograph.

6. Apparatus in accordance with claim 3 wherein the said ion source system comprises a source of high velocity particles that dissociate the molecules present in the output from the said chromatographic column, and wherein said apparatus includes means for accelerating said dissociation products through a suitable potential.

7. Apparatus in accordance with claim 6 wherein said high velocity particles are cesium 8. Apparatus in accordance with claim 3 wherein the said ion source system comprises a radio frequency ion source having an arc chamber in which the molecules that leave the chromatograph column are dissociated.

9. Apparatus in accordance with claim 8, including means for introducing a support gas into the ion source to allow the said source to operate continuously.

10. Apparatus in accordance with claim 9, wherein the support gas is oxygen.

11. Apparatus in accordance with claim 8, including means for extracting positive ions from the said ion source and a succeeding charge changing canal adapted to convert said positive ions to negative polarity.

12. Apparatus in accordance with claim 8, including means for extracting negative ions directly from the said arc chamber.

13. Apparatus in accordance with claim 3, wherein the said molecular dissociation is effected by high temperature pyrolysis.

14. Apparatus in accordance with claim 3, wherein the said particle detector is a solid state detector.

* * * * *